United States Patent [19]
Pötzschke et al.

[11] Patent Number: 5,042,947
[45] Date of Patent: Aug. 27, 1991

[54] SCRAP DETECTOR

[75] Inventors: Manfred Pötzschke, Kronberg; Hans-Peter Sattler, Bad Homburg; Kristian Hohla, Munich, all of Fed. Rep. of Germany; Thomas R. Loree, Los Alamos, N. Mex.

[73] Assignee: Metallgesellschaft Aktiengesellschaft, Frankfurt am Main, Fed. Rep. of Germany

[21] Appl. No.: 588,496

[22] Filed: Sep. 24, 1990

Related U.S. Application Data

[63] Continuation-in-part of Ser. No. 202,200, Jun. 3, 1988, abandoned.

[30] Foreign Application Priority Data

Jun. 4, 1987 [DE] Fed. Rep. of Germany ....... 3718672

[51] Int. Cl.$^5$ ..................... G01N 21/63; G01N 21/85
[52] U.S. Cl. .................................... 356/318; 209/579
[58] Field of Search ..................... 356/317, 318, 313; 250/458.1, 459.1, 461.1; 209/578, 579

[56] References Cited

U.S. PATENT DOCUMENTS

| | | | |
|---|---|---|---|
| 4,111,556 | 9/1978 | Grisar et al. | 356/313 X |
| 4,641,968 | 2/1987 | Grandy | 356/313 |
| 4,730,922 | 3/1988 | Bach et al. | 356/317 X |

FOREIGN PATENT DOCUMENTS

| | | | |
|---|---|---|---|
| 2565347 | 12/1985 | France | 250/461.1 |
| 2067753 | 7/1981 | United Kingdom . | |

OTHER PUBLICATIONS

Applied Spectroscopy, Band 41, Nr. 4, May/Jun. 1987, pp. 572–579, Soc. for Applied Spectroscopy, Frederick, Maryland, U.S.; D. A. Cremers.
Applied Spectroscopy, Band 40, Nr. 4, May/Jun. 1986, pp. 491–494, Soc. for Applied Spectroscopy, Frederick, Maryland, U.S.; J. A. Millard et al.
EOSD Elektro-Optical Systems Design, Band 14, Nr. 10, Oct. 1982, pp. 35–41, Chicago, Illinois, U.S.; T. R. Loree et al.
Navy Technical Disclosure Bulletin, Band 10, Nr. 1, Sep. 1984, pp. 97–101, Arlington, Virginia, U.S.; C. E. Bell et al.
Loree, T. R., Radziemski, L. J.: The Identification of Impurities in Metals by Laser-induced Breakdown Spectroscopy, Proc. Tech. Program-Electro-Opt.-/Laser Conf. Expo 1081, pp. 28–33.

Primary Examiner—Vincent P. McGraw
Attorney, Agent, or Firm—Felfe & Lynch

[57] ABSTRACT

Disclosed is a process and apparatus to analyze metal particles to determine their composition and to generate a sorting signal. The particles are exposed to a pulsed laser beam by which they are partly vaporized to form a plasma so that the particles are cleaned and the cleaned area is subsequently partially vaporized by a pulsed laser beam to form a plasma. The spectral lines of the plasma are inspected for an identification of the composition of the metal particles. The required inspection rate of 30 particles per second can readily be achieved or even exceeded if a defined narrow wavelength range or a defined wavelength is filtered from the total radiation that is emitted by the plasma and the intensities of the filtered partial radiations are related to each other to obtain ratios, which are compared with adjustable limiting values. A sorting signal is derived from the result of said comparison. The inspection rate can be improved in that the partial radiation is subjected to a comparison only for a defined interval of time.

20 Claims, 1 Drawing Sheet

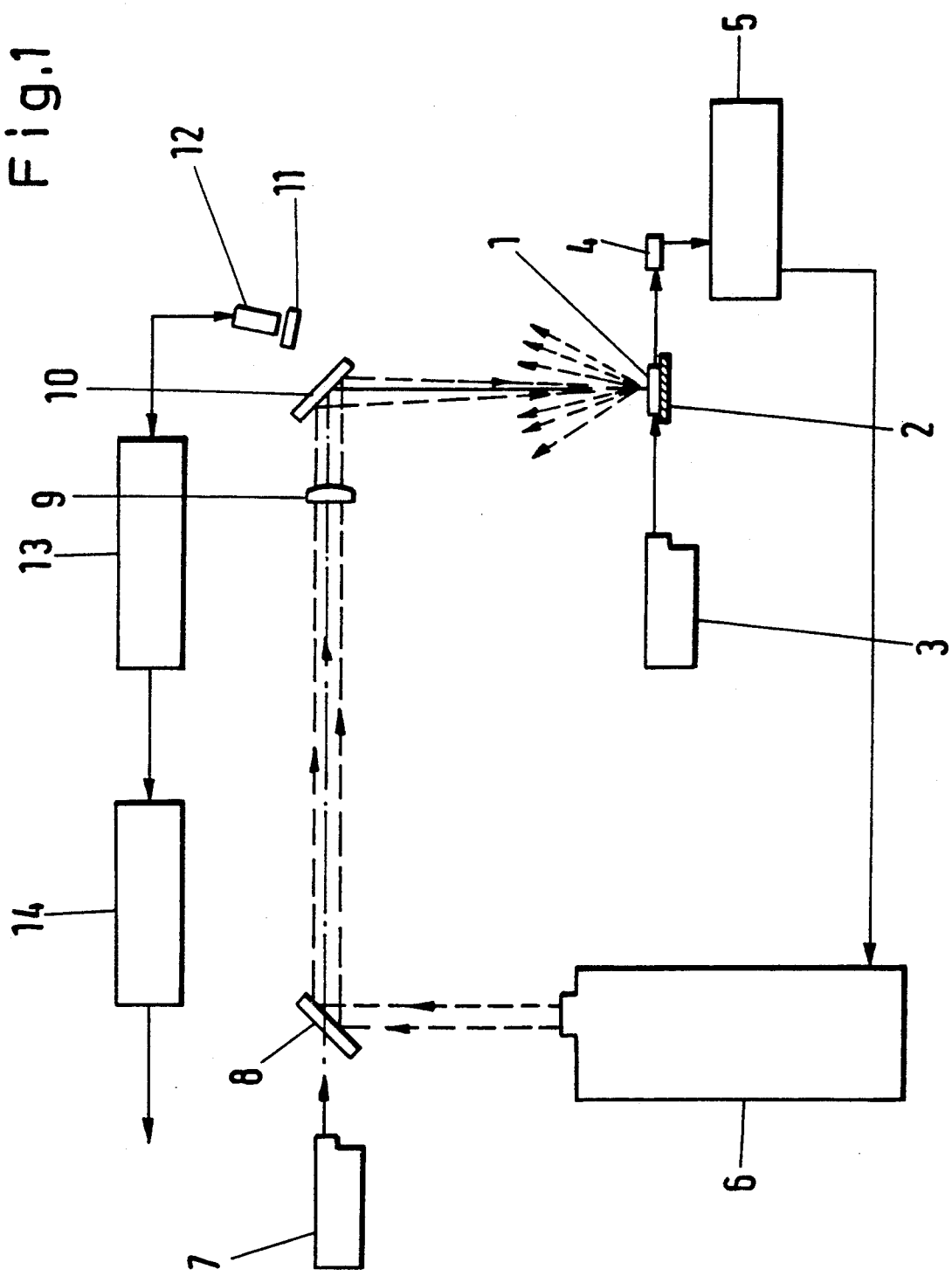

SCRAP DETECTOR

This application is a continuation-in-part of the application having Ser. No. 202,200 filed June 3, 1988 now abandoned.

DESCRIPTION

The present invention is in a process of analyzing metal particles for their chemical composition and for generating a sorting signal, so the particles are partly vaporized to form a plasma and the spectral lines of the plasma are analyzed for an identification of the composition of the metal particles.

The known laser-induced breakdown spectroscopy (LIBS) processes are based on the classical spectroscopic process developed by Fraunhofer. In the known processes an electric arc is struck between the material to be analyzed and an electrode, sample material is vaporized and the resulting white light is dispersed by diffraction in a grating. A comparison of the spectrum formed by diffraction with reference spectra and/or a measurement of the wavelength and intensity of individual spectral lines may then be utilized for a qualitative and quantitative determination of the elements contained in the inspected sample. Such a determination can take from minutes to hours depending on the information sought.

In the known LIBS processes a laser beam rather than an electric arc is used and the spectrum, or part of the spectrum, formed by diffraction is detected by a diode array, the output of which is utilized in a multichannel analyzer. (See also Loree, T. R., Radziemski, L. J.: The identification of impurities in metals by laser-induced breakdown spectroscopy", Proc. Tech. Program-Electro-Opt./Laser Conf. Expo 1081, 28–33).

In that process an analysis can be performed within 1 to 2 seconds, which is sufficiently fast for numerous applications but is too slow for a sorting at a high throughput rate, for instance, in the sorting of shredder scrap. In that case the ferromagnetic fraction is removed by magnetic separation, the non-metallic fraction is separated by sink-float processes and residual scrap is left, which consists of lumps and is composed of about one half of aluminum with the remainder being substantially of zinc, copper, lead and special steel. That unsorted residual scrap has a value from 700.- to 800 DM (Deutschmarks) per 1000 kg and about 2000 DM per 1000 kg when sorted. Since about 170,000 metric tons of such residual scrap are recovered per year in the Federal Republic of Germany alone, the value which can be added by separating the scrap into its individual components or into reusable groups of components is of an order of 200 million DM per year.

Various separating processes have already been proposed in efforts to permit realization of this added value. However, none of these processes has thus far been technologically and economically successful.

It is an object of the invention to improve the process defined first hereinbefore so that it can be used for a sorting at a high throughput rate, e.g., in the sorting of residual scrap outlined hereinbefore. In that case, particles having an average size of from 15 to 65 mm must be separated at a rate of at least 30 particles per second and the cost of the analysis of each particle must be distinctly lower than the value which can be added per particle.

SUMMARY OF THE INVENTION

The above objects and others are obtained by the process of the invention.

In the process of the invention the surface of the metal particles is partly cleaned by laser irradiation and a laser pulse is directed to the purified area to produce a plasma which is characteristic of the composition of the metal particle. Predetermined, selectable wavelengths are filtered from the total radiation of the plasma. Numerical ratios are derived from the radiation intensities of the filtered wavelengths, and a sorting signal is generated in dependence on the comparison of said ratios with adjustable limiting values.

In accordance with further features of the invention, predetermined narrow wavelength ranges rather than individual wavelengths are filtered and/or the radiation of the plasma is used for the analysis only for a predetermined time. The vaporization products formed by the laser irradiation effected for cleaning are suitably removed before the laser is fired to produce a characteristic plasma. More than one ratio may be derived and a plurality of predetermined limiting values may be used for the comparison.

For an analysis of metal particles which differ in size and shape, it is desirable to use a laser optical system which is so designed that the result of the measurement is independent of the distance between the laser source and the particle surface if that distance varies within a defined range. The pulsed laser beam may be initiated by a trigger signal which is generated in response to the entrance of the metal particle into the inspection path. The metal particles may be caused to traverse more than one inspection path in succession.

The evaluation of all measured values and obtained data and the generation of the desired sorting signal are preferably electronically performed. Finally, the process is preferably carried out in such a manner that the plasma radiation generated by the first laser pulse is directed to a metal particle to clean the same and is examined for wavelengths characteristic of aluminum. If the presence of aluminum is detected, the metal particle is not subjected to further laser pulses.

The present invention is also in an apparatus for carrying out the process of the invention and includes means for transporting the singled metal particles along an inspection path; a trigger signal generator comprising a trigger detector and trigger electronics for generating a trigger signal in response to the entrance of a particle into the inspection path; means for partly cleaning the surface of the metal particles by laser beams; a laser for generating pulsed laser beams; one or more spectral filters and spectral detectors associated with the respective filters; electronic circuitry for evaluating and comparing the spectral intensities which have been obtained; and a computer for processing the measured values and data which have been obtained and for generating a sorting signal.

The various features of novelty which characterize the invention are pointed out with particularity in the claims annexed to and forming a part of this specification for a better understanding of the invention, its operating advantages and specific objects obtained by its use, reference should be had to the accompanying drawing and descriptive matter in which there is illustrated and described a preferred embodiment of the invention.

BRIEF DESCRIPTION OF THE FIGURE

FIG. 1 shows an arrangement of apparatus for carrying out the process of the invention.

DESCRIPTION OF PREFERRED EMBODIMENT

Referring to FIG. 1, a belt conveyor 2 moves metal particles 1 along an inspection path which runs perpendicular to the plane of the FIGURE. A trigger laser 3 is provided with a trigger detector 4 and electronic trigger circuitry 5 for detecting the arrival of a metal particle and generating a start signal. A pulsed laser 6 generates a laser beam. The generated laser beam partially cleans the sample material. The beam is directed onto the metal particles 1 by a mirror 8, a focusing lens 9 and mirror 10. The beam is also used for analysis of the sample.

The apparatus also includes a spectral detector 12, which is provided with a pre-arranged spectral filter 11 and an electronic detector circuitry 13. The electronic detector circuitry 13 controls the measuring intervals of the spectral detector 12 and obtains computer-readable measured value data. An evaluating computer 14 derives the ratios of the measured values and compares the derived ratios with predetermined limiting values and generates one or more signals for the control of a sorting apparatus.

There is also an orienting laser 7, which emits a visible laser beam. The beam is focused on the same inspection point as the laser beam of the pulsed laser 6. Alternatively, a second pulse laser may be provided for partly cleaning the metal particles by means of laser pulses.

By an apparatus, not shown, for singling the metal particles 1 the belt conveyor 2 is fed with particles at an average rate of 30 particles per second. The belt 2 feeds the metal particles 1 at a corresponding velocity along the inspection path. When a metal particle enters the optical path of the trigger laser 3, the trigger detector 4 responds by causing the electronic trigger circuitry to generate a start signal for firing the pulsed laser 6. The laser 6 generates a beam which causes the metal particle 1 to be partly cleaned in that it is partly vaporized to form a plasma by means of a predetermined number of laser pulses. A predetermined number of additional laser pulses generates a plasma which is analyzed to determine the metal particle composition. The radiation emitted by that plasma is detected by the spectral detector 12 after a major part of the radiation from the plasma has been eliminated by the spectral filter 11, which transmits only a defined narrow wavelength range. The electronic detector circuit 13 causes the spectral detector 12 to detect the radiation from the plasma only for defined intervals of time so that the background noise of the radiation from the plasma will be minimized and the spectra can be more accurately identified.

If an interval amounting to one-thousandth of a second is available for each inspection, that time interval is utilized approximately as follows in the process in accordance with the invention.

About $5 \times 10^{-5}$ seconds pass from the entrance of the metal particle into the beam of the trigger laser until the "shot" of the pulsed laser. Since the laser shot takes only about $1 \times 10^{-8}$ seconds, the "cleaning" is completed after about $5 \times 10^{-5}$ seconds. The time required for the laser shots used for the analysis is also virtually negligible. The succeeding waiting time before the spectral detector is enabled amounts to about $5 \times 10^{-7}$ seconds. $5 \times 10^{-6}$ seconds are available for the measuring operation proper. The total time required for the operations described thus far does not exceed $0.6 \times 10^{-4}$ seconds so that $9.4 \times 10^{-4}$ seconds are available for the computer evaluation. That time is more than sufficient for an evaluation.

The process also provides a time allowance for an operation in which the time interval between consecutive metal particles is distinctly less than 0.03 seconds because a much higher throughput rate is required.

For a better understanding of the timing which has been explained, it may be assumed that the theoretical inspection time interval of $10^{-3}$ seconds corresponds to a distance of 1 meter or 1000 millimeters. In that case a distance of 50 mm would correspond to the time from the entrance of the particle into the beam of the trigger laser and the laser shot. The shot time corresponds to a distance of only 0.1 mm, the waiting time to a distance of 0.5 mm and the measuring time to a distance of 5 mm. About 940 mm are then available for an evaluation.

In view of these short measuring times the result of the measurement is not affected by the movement of the metal particle during the analysis. In the selected arrangement the result of the measurement will also remain unaffected by the fact that the distances between the metal particles being inspected and the laser optical system are different because the metal particles differ in size within limits determined by a classification.

The pulsed laser 6 is preferably a UV-gas-laser. UV-gas-lasers produce plasma from the metal particles on which the pulses are focused, but do not produce plasma from the ambient air. This nearly completely avoids the influence on the analysis of elements not belonging to the sample.

Moreover, only UV-gas-lasers are able to produce spots of equal intensity and extension (of area) independently of repetition time. As the scrap particles are of different size (normally within the range of 15 to 65 mm) small pieces can and must be analyzed faster than larger ones. Therefore, repetition time from piece to piece is not constant but varies continuously and the laser has to be started (by a trigger signal) at different intervals. Other lasers may be started as fast as the UV-laser. However, spot intensity and extension cannot be kept constant, and the result is that the analyzing system receives signals which cannot be used for comparison with given standards. Only UV-gas lasers are able to give more than 10 shots/sec with a repetition time, which is necessary for scrap particles varying of different size. This permits a throughput of the apparatus of 30 metal particles per second.

Another important aspects of the invention is that the plasma of the leaning shot is removed prior to the start of the analyzing shot by application of an air jet. The velocity of the air jet is preferably at least about 10 m/sec. Without this, the analyzing shot would ignite the plasma cloud created by the cleaning shot, and would not produce a plasma of the cleaned metal surface of the particle.

It will be understood that the specification and examples are illustrative but not limitative of the present invention and that other embodiments within the spirit and scope of the invention will suggest themselves to those skilled in the art.

We claim:

1. A process of analyzing metal particles for their chemical composition by laser-induced breakdown spectroscopy and of generating a sorting signal, said process comprising:
  (1) irradiating the surface of a metal particle using a cleaning pulse from a first UV-gas-laser;
  (2) removing the plasma produced by the cleaning pulse using an air jet of at least 10 m/sec.;
  (b 3) producing a plasma by directing an analysis pulse from the first UV-gas-laser or another UV-gas-laser to the cleaned surface;
  (b 4) filtering predetermined, selectable wavelengths from the total radiation of the plasma produced by the analysis pulse;
  (5) measuring the radiation intensities of the filtered wavelengths; and
  (b 6) generating a sorting signal based on comparison of the measures of the radiation intensities with adjustable predetermined values.

2. The process of claim 1 wherein the filtering of the predetermined selectable wavelengths constitutes a filtering of a predetermined narrow wavelength range.

3. The process of claim 1 wherein the radiation of the plasma is used for the analysis for a predetermined time.

4. The process of claim 1 wherein more than one measurement of radiation intensity is derived and a plurality of predetermined limiting values are used for the comparison.

5. The process of claim 1 wherein the metal particles differ in size and shape.

6. The process of claim 1 wherein the laser is used with an optical system which provides a measurement independent of the distance between the laser source and the particle surface if that distance varies within a defined range.

7. The process of claim 1 wherein the laser is fired by a trigger signal which is generated in response to the metal particle entering into an inspection path.

8. The process of claim 1 wherein the metal particles traverse more than one inspection path in succession.

9. The process of claim 1 wherein all measured values and data and the generated sorting signal are by electronic means.

10. The process of claim 1 wherein the plasma radiation generated by the first irradiation to clean the metal particle surface is examined for wavelengths characteristic of aluminum.

11. The process of claim 10 wherein the analysis laser pulse is discontinued if aluminum is detected.

12. The process of claim 1 wherein the particles are processed at a rate of at least 30 particles per second.

13. The process of claim 12 wherein the particles have an average size generally in the range of about 15 to 65 mm.

14. In a process of analyzing metal particles having an average size of from 15 to 65 mm and at a rate of at least 30 particles per second for their chemical composition by laser-induced breakdown spectroscopy (LIBS) and of generating a sorting signal, the improvement of
  (1) using a pulsed UV-gas-laser;
  (2) irradiating a surface of the metal particles to partially clean the surface;
  (3) removing the plasma produced by the cleaning pulse with an air jet of at least 10 m/sec;
  (4) producing a plasma by directing a laser pulse to the cleaned surface, the plasma being characteristic of the metal particle composition;
  (5) filtering predetermined, selectable wavelengths from the total radiation of the plasma;
  (6) deriving numerical ratios from the radiation intensities of the filtered wavelengths; and
  (7) generating a sorting signal in dependence on a comparison of said derived ratios with adjustable limiting values.

15. Apparatus for carrying out the process of claim 14 comprising:
  means for transporting metal particles along an inspection path;
  a trigger signal generator having a trigger detector and trigger electronics for generating a trigger signal in response to the entrance of a particle into the inspection path;
  means for partly cleaning the surface of the metal particles by irradiation with a first UV-gas-laser pulse;
  jet means for withdrawing plasma formed when cleaning the particle by irradiation, said jet means having velocity of at least 10 m/sec;
  means for irradiating the particle with a second UV-gas-laser pulse to produce a characteristic plasma;
  at least one spectral filter means and a corresponding number of spectral detector means associated with each spectral filter means;
  electronic circuitry for evaluating and comparing the spectral intensities which have been obtained by said spectral detector means;
  computer means for processing the measured values and data which have been obtained and for generating a sorting signal.

16. The process of claim 14 wherein the predetermined selectable wavelengths filtered are in a predetermined range of wavelengths.

17. The process of claim 14 wherein the radiation of the plasma is used for the analysis for a predetermined time.

18. The process of claim 14 wherein more than one ratio is derived and a plurality of predetermined limiting values are used for the comparison.

19. The process of claim 14 wherein the laser is fired by a trigger signal which is generated in response to the metal particle entering into an inspection path.

20. The process of claim 14 wherein the metal particles traverse more than one inspection path in succession.

* * * * *